US00PP11063P

United States Patent [19]

Moore

[11] Patent Number: Plant 11,063

[45] Date of Patent: Sep. 14, 1999

[54] MINIATURE ROSE PLANT NAMED 'MORSIXTY'

[76] Inventor: Ralph S. Moore, 2519 E. Noble Ave., Visalia, Calif. 93292

[21] Appl. No.: 09/004,843

[22] Filed: Jan. 9, 1998

[51] Int. Cl.[6] ..... A01H 5/00

[52] U.S. Cl. ..... Plt./116

[58] Field of Search ..... Plt./116, 121, 123, Plt./128

[56] References Cited

U.S. PATENT DOCUMENTS

P.P. 6,673 3/1989 Williams ..... Plt./116
P.P. 7,187 3/1990 Bennett ..... Plt./116

*Primary Examiner*—Howard J. Locker

[57] ABSTRACT

This invention relates to a new and distinct cultivar of miniature rose, primarily identified by the mauve (lavender) color of its petals and double flowers.

1 Drawing Sheet

The present invention relates to a new and distinct cultivar of hardy, dwarf, bush type rose plant of the miniature class. The cultivar being primarily characterized—as to novelty by its mauve (lavender) color and double flowers.

The cultivar is further characterized by:

An abundance of bloom, with flowers usually borne in small clusters (sometime singly) to the stem.

Slight Fragrance.

A plant of vigorous, rounded to compact, bushy growth shape, with semi-glossy foliage with pointed leaflets; the buds and flowers being similar in form to 'Lavender Jewel' (miniature rose; U.S. Plant Pat. No. 4,480) but differing in color, being a more clear shade of lavender and without the (sometimes) reddish tints on petal edges.

A plant which grows and blooms satisfactorily both in greenhouse and outdoors; with repeat bloom, is good for growing in pots, and provides excellent garden decoration as well as cut flowers.

The present cultivar of miniature rose was originated by me at my nursery, located at Visalia, Calif., under conditions of careful control and observation, as a result of a cross between 'MORjoyc' ('Joycie', miniature rose; U.S. Plant Pat. No. 7,055) as the seed parent and 'MORchermag' ('Cherry Magic', miniature rose, U.S. Plant Pat. No. 7,061) as the pollen parent.

As compared to 'Lavender Jewel', the present cultivar has larger size foliage and flowers and plant is less thorny.

Subsequent to my origination of the cultivar I successfully asexually reproduced this new cultivar at my nursery, located as aforementioned, by budding as well as by cuttings; the reproductions have run true in all respects.

The photograph illustrates the cultivar including the foliage, buds and flowers.

Plant part coloration illustrated is as true as reasonably possible to attain in photographic illustrations of this type.

Referring now specifically to the new and distinct cultivar of miniature rose plant, the following is a detailed description thereof in outline; all major color plate identification being by reference to the *R.H.S. Colour Chart* (Royal Horticultural Society) except where common terms of color definition are employed.

Type: Hardy; dwarf; upright; seedling; greenhouse; outdoors; cut flowers; garden decoration; potted plant.

Class: Miniature: Cultivar indentification: 'MORsixty' (commercial synonym: DIAMOND ANNIVERSARY).

Flowers borne: Usually in loose clusters, sometimes singly, on sturdy, wiry stems.

Quantity of bloom: Abundant both outside and inside greenhouse.

Bud:

*Peduncle.*—Medium length; slender but sturdy; erect; medium green, near Green Group 138A, sometimes tinted bronze (outdoors); nearly smooth.

*Before calyx breaks.*—Size-small.

*Form.*—Pointed, with several small foliaceous appendages on surface of the bud; with foliaceous parts extending beyond the tip of the bud equal to one half or more than one half of its length.

*Color.*—Medium green, near Green Group 138A, occasionally tinted with bronze (outdoors). As calyx breaks — Color — mauve, near Red-Purple Group 74C. Opening — Opens well in all weather.

Bloom:

*Size when fully open.*—Small, averaging about 40 mm or 1¾".

*Petalage.*—Double — averaging about 40 petals, arranged regularly plus several small petaloids.

*Form.*—Full, high centered at first, becoming rounded with petals rolled loosely outward and downward. Fully opened flowers show stamens (not shown in photo).

*Sepals.*—Permanent; spear shaped; recurved.

*Behavior.*—Opens well in all weather; spent petals or flowers drop off.

*Flower longevity* (*August* 1997).—Plant in pot — 4 to 6 days or longer. Cut flowers at living room temperature — 4 to 5 days.

Petals: Fairly thick; satiny on inside and on outside surface.

*Shape.*—Outside petals: broad lanceolate, nearly round with small acute tip. Intermediate: broad lanceolate rounded or nearly round with short acute tip. Inside: broad lanceolate with rounded or acute tip.

*Color* (Newly opening flower from plant grown in plastic greenhouse in October, 1997, Visalia, Calif. (Photograph taken October 1997)).—Outside petal: Outside surface — mauve near Red-Purple Group 74C blending into yellow at petal base. Inside surface — near Red-Purple Group 74D blending into yellow at petal base. Intermediate petal: Outside surface similar to outside petal; Inside surface similar to intermediate petal. Inner petal: Outside surface similar to intermediate petal. Inside surface similar to intermediate petal. NOTE: The lavender color may be suffused with yellow, giving a lavender-tan effect, especially in the Fall and in cooler weather.

*General color effect.*—Newly opened flowers — clear all over lavender. 3 days open — color similar to newly opened flower, but lighter and less bright.

Flower (petal) color becomes progressively lighter as the flowers age.

Reproductive organs:

*Stamens.*—Moderately abundant, arranged regularly about the pistil.

*Filaments.*—Fairly short, yellow.

*Anthers.*—Well formed, yellow.

*Pollen.*—Moderate.

*Pistils.*—Average number.

*Styles.*—Long; near white; bunched.

*Ovaries.*—All enclosed in calyx.

*Hips.*—Usually none.

*Seed.*—None.

Foliage:

*Leaves.*—Compound of five (sometimes 3 or 7) leaflets; medium small); leathery; semi-glossy.

*Leaflets.*—Shape: Broad lanceolate; apex acute; base — rounded. Color: Medium green (can be as dark as Green 137A); new growth — normal (medium) green sometimes tinted reddish. Rachis: Medium strength; upper side smooth; grooved; underside may have several small thorns (or claws). Stipules: Medium to long length; medium width; medium to short length narrow points which turn out usually at about 45° or less. Color similar to leaflets.

*Habit.*—Dwarf; bush; upright; much branched. Plant height: 40–45 cm. Plant spread: 35–40 cm.

*Growth.*—Vigorous; internodes short.

*Canes.*—Medium slender; sturdy.

*Main stems.*—Color: Medium green, near Green Group 138A.

*Thorns.*—Few of small size and length, usually straight, color: brown. Hairs — none.

The miniature rose plant and its flowers as heretofore described may vary in slight detail due to climate, soil and cultural conditions under which the cultivar may be grown; the present description being of the cultivar as grown at Visalia, Calif.

The following is claimed:

1. A new and distinct cultivar of rose plant of the miniature class, of hardy, dwarf, bushy, much branched habit substantially as illustrated and described, characterized by buds and flowers, basically Mauve (lavender), the bud being pointed in the early stage, resembling in form 'Lavender Jewel' (miniature), with the open flower being double and rounded with 40 or more petals; and further characterized by a plant of compact, vigorous, upright shape with main stems and shoots of less than average thorniness, the said plant being easy to propagate from soft-wood cuttings with an abundance of small, semi-glossy foliage, the flowers being usually borne in small clusters on medium length stems.

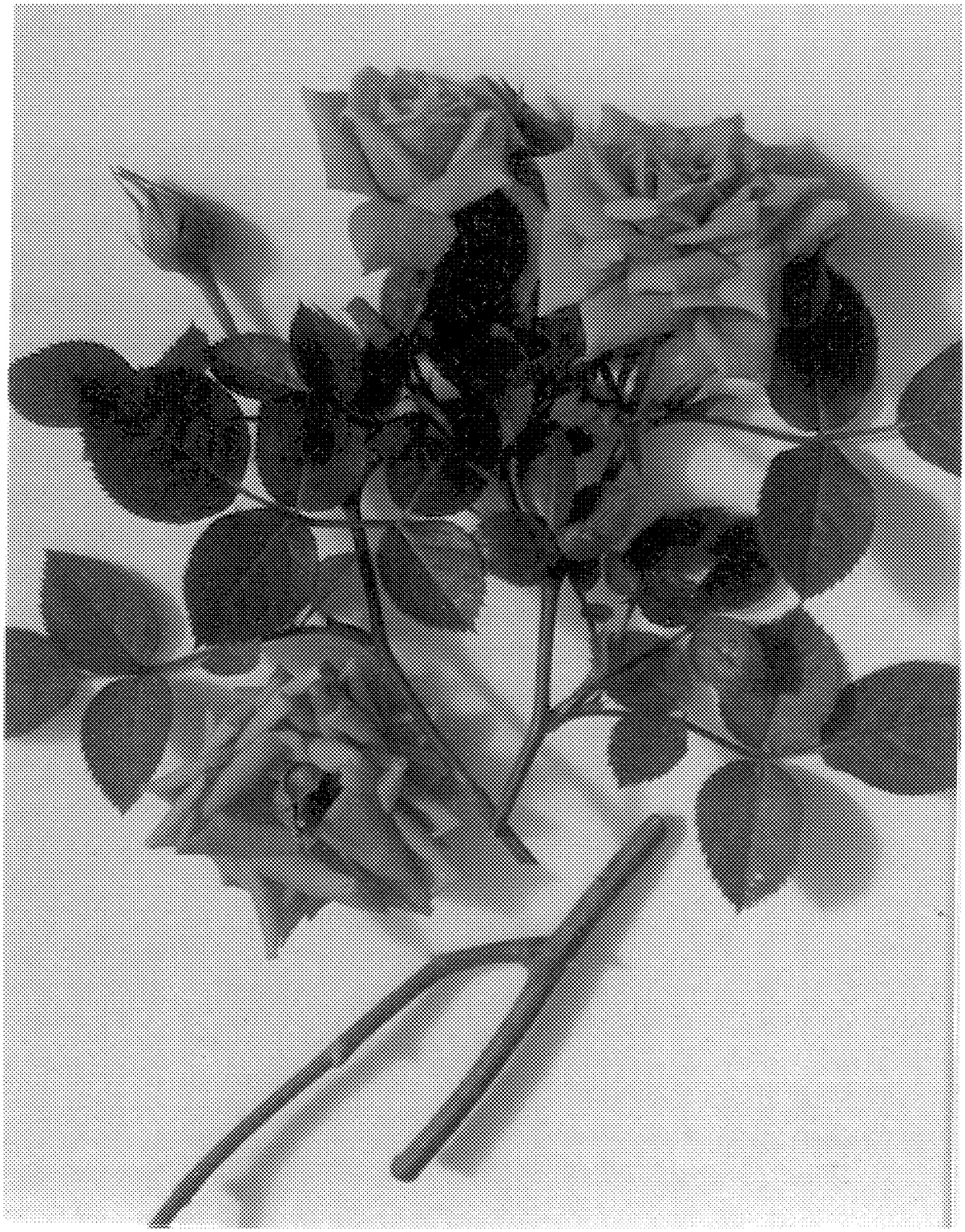

* * * * *